United States Patent
Sternberg et al.

[11] Patent Number: 5,879,292
[45] Date of Patent: Mar. 9, 1999

[54] BANDAGE INCLUDING DATA ACQUISITION COMPONENTS

[75] Inventors: Edward A. Sternberg, 2527 N. Lefeber Ave., Wauwatosa, Wis. 53213; Jan-Tjeerd H. N. de Faber, Rotterdam, Netherlands

[73] Assignee: Edward A. Sternberg, Wauwatosa, Wis.

[21] Appl. No.: 948,123

[22] Filed: Oct. 9, 1997

[51] Int. Cl.⁶ .............................. A61B 5/00; G08B 21/00
[52] U.S. Cl. ........................................................ 600/300
[58] Field of Search .................... 600/382–394, 600/300; 602/41–47, 74; 604/361, 318; 128/885, 886, 897–898

[56] References Cited

U.S. PATENT DOCUMENTS

| | | | |
|---|---|---|---|
| 3,092,103 | 6/1963 | Mower ..................................... | 128/858 |
| 3,633,567 | 1/1972 | Sarnoff . | |
| 3,832,993 | 9/1974 | Clipp . | |
| 4,193,068 | 3/1980 | Ziccardi .................................. | 340/604 |
| 4,213,463 | 7/1980 | Osenkarski . | |
| 4,502,491 | 3/1985 | Ender et al. . | |
| 4,583,546 | 4/1986 | Garde . | |
| 4,605,010 | 8/1986 | McEwen . | |
| 4,776,331 | 10/1988 | Simjian . | |
| 4,807,640 | 2/1989 | Watson et al. .......................... | 600/534 |
| 4,869,265 | 9/1989 | McEwen . | |
| 4,951,658 | 8/1990 | Morgan et al. . | |
| 5,469,145 | 11/1995 | Johnson ............................. | 128/886 X |
| 5,557,263 | 9/1996 | Fischer et al. .......................... | 340/605 |
| 5,579,765 | 12/1996 | Cox et al. . | |
| 5,584,853 | 12/1996 | McEwen ................................ | 606/201 |
| 5,760,694 | 6/1998 | Nissim et al. ...................... | 128/886 X |

OTHER PUBLICATIONS

"Amblyopia", deFaber et al., Current Opinion in Opthalmology, 1996, 7; V: 8–12.
"Smart Sensors", Travis, EDN May 9, 1996, pp. 57–65.
"Compliance in amblyopia therapy: objective monitoring of occlusion", Fielder et al., British Journal of Optholmology, 1995; 79: 585–589.

*Primary Examiner*—John P. Lacyk
*Assistant Examiner*—Samuel Gilbert
*Attorney, Agent, or Firm*—Andrus, Sceales, Starke & Sawall

[57] ABSTRACT

A bandage including a self-contained microcontroller that can sense, record, process and/or report information concerning the use of the bandage. The bandage includes a microcontroller contained within the padded portion of the bandage. A sensor is connected to the microcontroller and generates a signal based on whether the bandage is attached to a patient. The signal generated by the sensor is received by the microcontroller and analyzed and/or recorded by the microcontroller. The microcontroller operates to analyze the information from the sensor, thereby generating and reporting clinically useful information as to the status of the bandage. The bandage of the invention includes a data transfer port such that the bandage can be attached to an external computer and information transferred to or from the bandage.

29 Claims, 3 Drawing Sheets

BANDAGE INCLUDING DATA ACQUISITION COMPONENTS

BACKGROUND OF THE INVENTION

The present invention relates to a bandage having internal components that record, process, store and/or deliver information concerning the usage of the bandage. More specifically, the invention relates to an eye patch that includes a microcontroller which records, processes, and delivers information concerning the times the eye patch was worn by a patient.

Amblyopia, often referred to as "lazy eye", generally refers to poor vision in one eye as a result of improper development during infancy and childhood. Amblyopia is the most common vision defect of childhood, occurring in approximately 1%–5% of the population. Amblyopia can be caused by any condition that affects normal bilateral usage of the eyes and normal visual development during childhood. In many cases, the conditions associated with amblyopia may be inherited. The most common cause of amblyopia is a misalignment of the eyes because of muscle problems. Other causes include significant differences in focusing between the two eyes, high amounts of astigmatism, retinal defects, and other visual disorders such as cataracts. Generally, amblyopia occurs when the child relies exclusively on his or her better eye for vision. For example, when the child has one crossed eye because of muscle problems, the crossed eye effectively "turns off" to avoid double vision, resulting in the child using only the better eye. As use of the crossed eye diminishes, the muscles and parts of the brain required for its normal function weaken, reinforcing the amblyopia, as a feed-forward process.

If amblyopia is detected early in the child's development, treatment is often very effective (success rates up to 93%) in correcting the amblyopia. The best approach to manage amblyopia is to detect the disfunction before the age of two and break the feed-forward spiral of amblyopic disuse. If amblyopia starts, it can most effectively be cured if children are adequately treated before the ages of six to seven years. To correct amblyopia, a child must be made to use the weak eye instead of relying only upon the strong eye. This is done by occlusion therapy, which involves patching or covering the strong eye for several hours during the day, often for weeks to as long as years, to force the weak eye into usage.

In order to treat amblyopia, a critical factor is patient compliance. Since amblyopia must be treated when children are under the age of six, it is often difficult for the physician to determine whethe r the patient is following the prescribed occlusion therapy. In some studies, the patient compliance rate has been found to be around 50%. Thus, although specific patching regimes can be prescribed, until now, their effectiveness has been difficult to determine. Presently, patient compliance is typically measured by clinical attendants or by a parental occlusion log book which details the amount of time a child is wearing the eye patch. While an occlusion log book is an attempt to monitor occlusion, it suffers from several weaknesses, such as bias of the third-party recorder and the inability to monitor the patient for the entire duration of the therapy.

Recently, an occlusion dose monitor (ODM) has been developed to help the physician more accurately determine patient compliance. The ODM is a portable datalogger that can measure the time an eye patch is in contact with the skin by means of a reduced resistance between two miniature electrocardiogram electrodes. The datalogger is worn in a shoulder bag by the patient and includes a pair of leads connected between the datalogger and the eye patch. When a patient is wearing the ODM, the physician can recover information from the datalogger as to when the eye patch was worn, giving the physician an objective measurement of how accurately his therapy has been followed. Before the ODM, it was not possible for the physician to distinguish between poor patient compliance and physiologic non-responsiveness to occlusion. By using an ODM, however, the physician can objectively monitor the period of time the eye patch was worn by the patient and adjust his dose accordingly.

Although the discussed ODM has been used to measure patient compliance, the datalogger contained in a shoulder bag is cumbersome and inconvenient for an otherwise active child to use, especially if occlusion therapy is prescribed for an extended continuous period of time. Additionally, the externally worn datalogger is subject to physical damage when worn by a young child who is active or unconcerned with preventing damage to the datalogger. Finally, the datalogger can draw abnormal attention to the young patient, which increases the patient's resistance to treatment. Thus, it is readily apparent that a compact bandage or eye patch which includes small and unobtrusive components that can accurately record and store data concerning the status of the bandage and the patient would be a great advantage.

BRIEF SUMMARY OF THE INVENTION

The present invention is a bandage that includes components capable of recording and/or analyzing data related to the use of the bandage. The components are contained within the bandage so that it can be worn by a patient with minimal interference in the patient's normal activities.

The bandage of the invention is particularly useful as an eye patch and includes a pad member that is positionable in contact with the patient. Preferably, the pad is positioned over an eye of the patient to completely block that eye's sight. A microcontroller is embedded and completely contained within the pad. A power supply is also completely contained within the pad such that the power supply enables the microcontroller.

The bandage of the invention includes a sensor that is connected to the microcontroller and provides a signal to the microcontroller related to the status of the pad. In one embodiment of the invention, the sensor provides a first signal when the pad is in contact with the patient, and provides a second signal when the pad is out of contact with the patient. The microcontroller includes a timer and memory that records when the signal from the sensor changes between the first signal and the second signal. By recording the changes in the signal from the sensor, the microcontroller records when the pad is attached to and removed from the patient. When the eye patch is used according to a doctor's instructions, the microcontroller functions to monitor and record the amount of time the eye patch is worn by the patient in an objective manner.

The bandage of the invention further includes a data transfer port formed in the pad between the microcontroller and the exterior of the pad. The data transfer port allows the bandage to be interrogated by an external computer such that the stored information in the microcontroller that is received from the sensor can be downloaded and analyzed to determine how the bandage was used by the patient.

By using the bandage of the invention, a physician can more accurately determine the period of time a patient wore the bandage. In this manner, the physician can determine whether the patient has complied with the physician's instructions.

It is an object of the invention to provide a bandage that includes internal components capable of monitoring and/or recording the status of the bandage and the patient. More specifically, it is an object of the invention to provide an eye patch that can monitor and record the amount of time the eye patch was worn by a patient.

It is another object of the invention to provide a bandage that includes self-contained components capable of recording information related to the use of the bandage. Finally, it is an object of the invention to provide a bandage which can be interrogated by an external computer to read and analyze the data acquired and stored by the bandage.

Other features and advantages of the invention may be apparent to those skilled in the art upon inspecting the following drawings and description thereof.

BRIEF DESCRIPTION OF THE DRAWINGS

The drawings illustrate the best mode presently contemplated of carrying out the invention.

In the drawings.

DETAILED DESCRIPTION OF THE DRAWINGS

Figure 1:
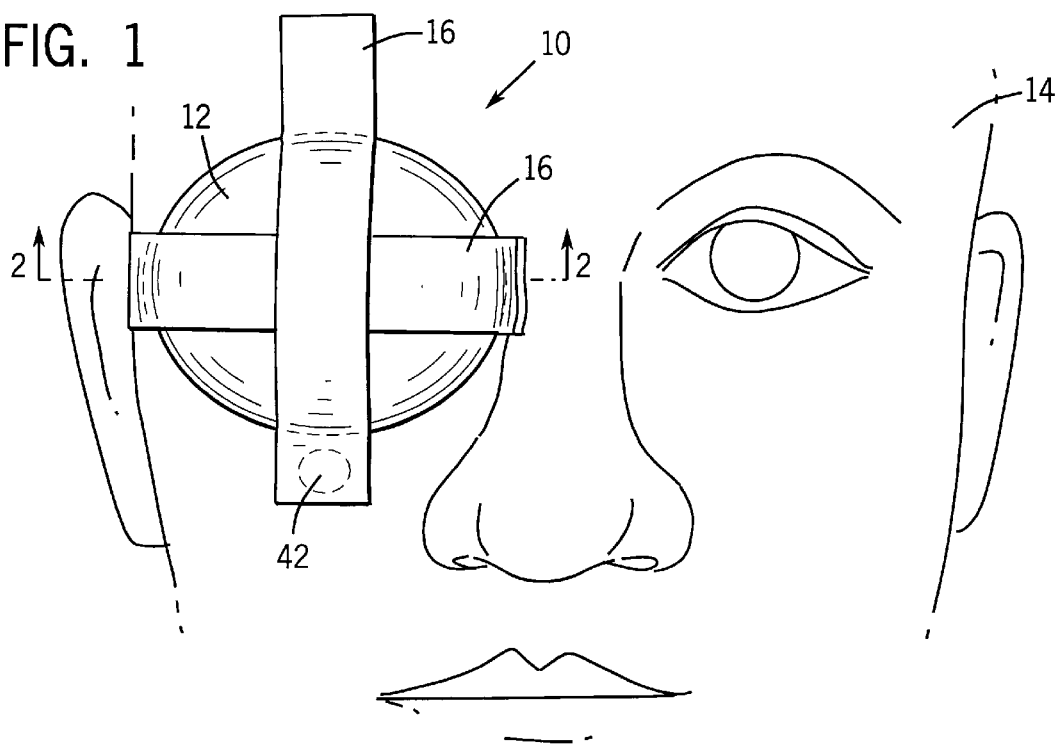
FIG. 1 is a front view showing the bandage of the invention as applied over the eye of a patient.

Referring first to FIG. 1, thereshown is the bandage of the present invention, generally referred to by reference numeral 10. In the preferred embodiment of the invention, the bandage 10 is an eye patch 12 that functions to block sight from one eye of a patient 14. Although the bandage 10 will be discussed as being the eye patch 12 in the present description, it should be understood that the bandage 10 could take a variety of different forms or be constructed from a variety of materials while still operating under the scope of the invention, as will be further detailed below. As can be seen in FIG. 1, the eye patch 12 is attached to the face of the patient 14 by a suitable attachment means, such as a pair of adhesive strips 16. The adhesive strips 16 each pass over the eye patch 12 and make contact with the face of the patient 14. Although the invention is described as having a pair of adhesive strips 16, it is contemplated by the inventors that the adhesive strips 16 could be replaced by a continuous adhesive border surrounding the outer edges of the eye patch 12. Further, it is contemplated by the inventors that the attachment means could take several forms, so long as a suitable means exists for holding the eye patch 12 in place on the patient's face.

In the preferred embodiment of the invention, the eye patch 12 is useful in occlusion therapy for treating visual disorders, most particularly amblyopia. Occlusion therapy is a well-known therapy for treating amblyopia and includes blocking the vision from the patient's good eye, thereby forcing the patient to use the amblyopic or weak eye exclusively. For the bandage 10 to work as the eye patch 12, the eye patch 12 must be sufficiently opaque such that the patient 14 is unable to see through the eye patch 12. Since the goal of the eye patch 12 is to prevent the patient 14 from having any vision out of their strong eye, the inventors contemplate an adhesive means completely surrounding the outer peripheral edges of the eye patch 12 to attach the eye patch 12 to the patient's face. A continuous adhesive strip surrounding the outer circumference of the eye patch 12 is contemplated as being the most effective attachment means, since the continuous adhesive strip would more effectively prevent the patient 14 from "peeking" out under the bottom of the eye patch 12 to use their good eye. Since the eye patch 12 is typically used on children under the age of 6, it is important to prevent the patient 14 from cheating and using their good eye for vision.

Figure 2:
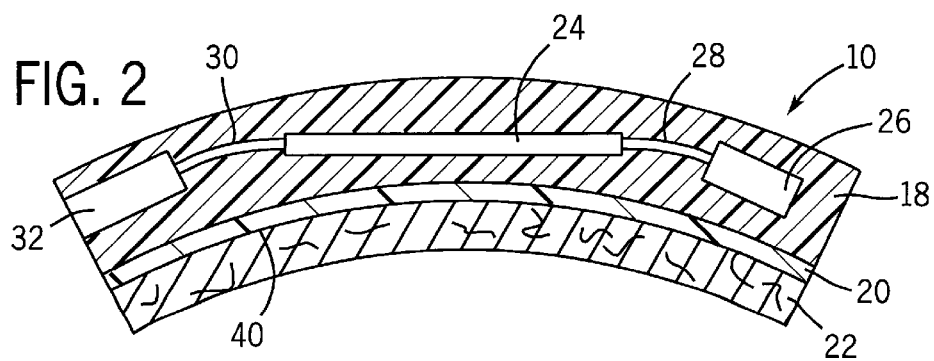
FIG. 2 is a section view taken along line 2—2 in FIG. 1 showing the data acquisition components internally mounted within a pad.
Figure 4:
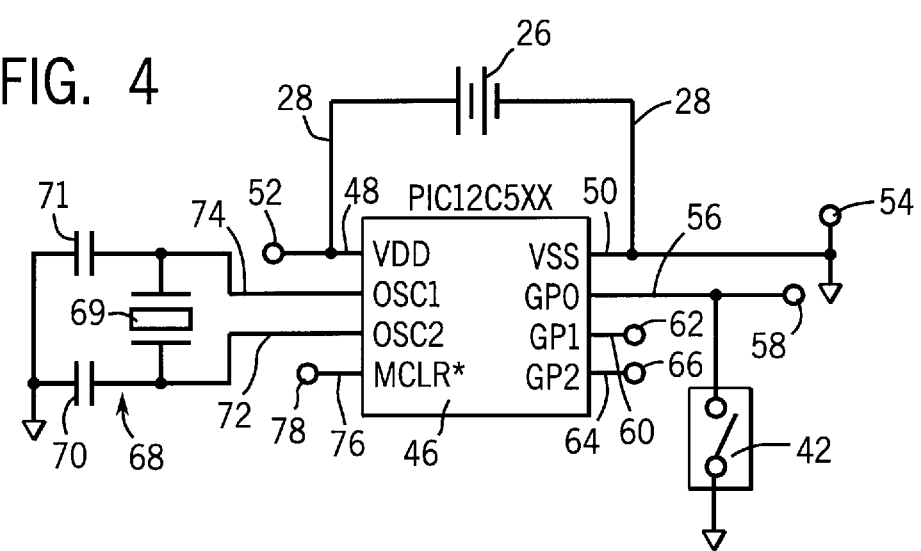
FIG. 4 is a detailed circuit diagram showing the internal circuitry used to acquire data and contained within the bandage.

FIG. 2 shows the internal configuration of the bandage 10 used as the eye patch 12. The eye patch 12 of the preferred embodiment generally includes three layers; an outer pad 18, a protective shield 20, and a cushion member 22. The outer pad 18 is a generally soft, cloth-like member having a series of internal components that gather and store data concerning the status of the bandage 10, as will be discussed in greater detail below. Specifically, the outer pad 18 surrounds a circuit board 24. The circuit board 24 includes a series of components, which are shown in FIG. 4, mounted on a flat circuit board having a size of approximately ½ inch by ½ inch. The components mounted on the circuit board 24 are connected to a power supply 26 by wires 28. Although the power supply 26 is shown as being located externally from the circuit board 24, it is contemplated by the inventors that the power supply could be attached to the circuit board 24 while still operating under the scope of the invention. As shown in FIG. 2, the power supply 26 is completely contained within the outer pad 18 along with the circuit board 24.

Figure 3:
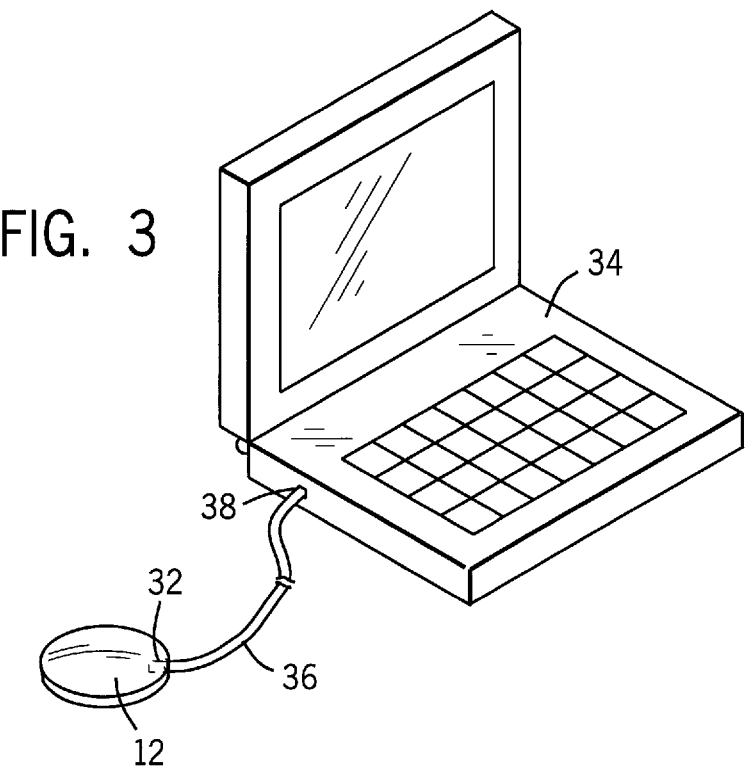
FIG. 3 is a perspective view showing the connection between the bandage of the present invention and an external computer.

The circuit board 24 is connected by further wires 30 to a data transfer port 32 such that information can be uploaded or downloaded from the components mounted to the circuit board 24. FIG. 3 schematically shows the eye patch 12 coupled to a computer 34 by a cable 36 extending between the data transfer port 32 and an input/output port 38 contained on the computer 34. Although FIG. 3 shows the computer 34 connected directly to the eye patch 12, it should be understood that a conventional interface component may be required between the computer 34 and the eye patch 12 to condition the signal from the eye patch 12. Additionally, it is presently contemplated by the inventors that the cable 36 could be replaced by other equivalent means for transferring data between the eye patch 12 and the computer 34, such as infrared or radio frequency communication. Along with being able to download information stored in the eye patch 12, the computer 34 can be used to program the components mounted to the circuit board 24 contained within the outer pad 18. In the preferred embodiment of the invention, the computer 34 could be a conventional personal computer capable of running a variety of commercially available programs used both to download information from the eye patch 12 and to program the components contained on the circuit board 24.

Referring again to FIG. 2, it can be seen that the outer pad 18 is connected to a protective shield 20 by any known adhesive means, such as a common adhesive bond between the cloth-like outer pad 18 and the protective shield 20. In one embodiment of the invention, the protective shield 20 is a polycarbonate lens having generally the shape shown in FIG. 1. Since the eye patch 12 is placed over the eye of a patient, it may be desirable to provide protection for the patient's eye.

In the preferred embodiment of the invention, a cushion member 22 is securely connected to the back face 40 of the protective shield 20. The cushion member 22 can be formed of any cushion-like material which will provide an increased level of comfort for the patient wearing the eye patch 12. Since the cushion member 22 will be in contact with the patient's skin, it is contemplated that the cushion member 22 will be a hypo-allergenic material typically used in commercially available bandages.

Although the eye patch 12 has been described as having a three layer construction to provide additional protection and comfort for the patient, it is contemplated by the inventors that the outer pad 18 could be used alone either as an eye patch 12 or for other purposes that will become readily apparent in the following discussion. In the preferred embodiment of the invention, the outer pad 18 is constructed of a generally opaque material such that the patient 14 is unable to see through the outer pad 18.

In addition to the components described and shown in FIG. 2, a sensor 42 is also connected to the circuit board 24 by a pair of wires. The sensor 42 is used to make a specific measurement as to the status of the outer pad 18 or the condition of the patient to which the outer pad 18 is attached. In the embodiment shown in FIG. 1, the sensor 42 is positioned between the adhesive strip 16 and the skin of patient 14 such that the eye patch 12 can be monitored by the internal components of the outer pad 18 to determine the duration of time the eye patch 12 is in contact with the patient 14. By placing the sensor 42 between the adhesive strip 16 and the patient 14, the sensor 42 provides information to the internal components contained within the outer pad 18 concerning the amount of time the eye patch 12 is worn by the patient.

In the preferred embodiment of the invention, the sensor 42 is a contact-sensitive switch that is in the closed position when the adhesive strip 16 is in contact with the patient. Specifically, the adhesive strip 16 holds the contact-sensitive switch in the closed position to generate a first signal when the eye patch 12 is applied to the patient 14. When the adhesive strip 16 is removed from the patient, the contact-sensitive switch opens and generates a second signal. Although the invention has been described as incorporating a contact-sensitive switch as the sensor 42, it is contemplated by the inventors that a wide variety of sensors and/or switches could be used as the sensor. For example, the sensor 42 could be a heat sensitive sensor, a tactile pressure sensor, an electrical switch that responds to skin resistance, or any other type of sensor which measures a variable important to the desired use of the bandage 10. When the sensor 42 is replaced by one of the contemplated alternatives, the signal generated by the sensor will vary between an upper limit and lower limit, rather than the ON and OFF state associated with the contact-sensitive switch as described above. In either case, the components mounted to the circuit board 24 are capable of receiving information from the sensor 42 and storing or processing such information.

It is contemplated by the inventors that the bandage 10 could be modified for a variety of purposes other than use as the eye patch 12. For instance, the bandage 10 could be modified such that the sensor 42 monitors the status of a wound to which the bandage 10 is applied. In this type of embodiment, the sensor 42 could be a pH sensor (or a monitor of oxygen saturation) that monitors the acidity (or the oxygen tension) of the wound to determine whether the wound is infected or healing. In any event, the internal components mounted to the circuit board 24 are capable of receiving data from the sensor 42 and storing or processing the data within the internal components mounted to the circuit board 24.

FIG. 4 shows a circuit diagram for the electronic components mounted to the circuit board 24. The electronic components are centered around a microcontroller 46. The microcontroller 46 is preferably a programmable microcontroller that can be programmed by an external programmer in a conventional manner. In the preferred embodiment of the invention, the microcontroller 46 is Part No. PIC12C509, sold by the Microchip Corporation. The factory assigned pin designations for the microcontroller 46 are shown in FIG. 4 for the ease of understanding. The microcontroller 46 can be programmed by a commercially available programming kit, such as Part No. DV003001-ND, also sold by Microchip. The programmer allows the user to program the microcontroller 46 by using software loaded onto a conventional PC.

The power supply 26 is connected to the microcontroller 46 by the wires 28 between the VDD pin 48 and the VSS pin 50. In the preferred embodiment of the invention, the power supply 26 is a small battery, such as a 3-volt lithium battery. The power supply 26 provides the required electrical power to run the microcontroller 46. In addition to being connected to the power supply 26, the VDD pin 48 and the VSS pin 50 are each connected to an output terminal 52 and 54, respectively. The output terminals 52 and 54 are each connected by a separate wire to the data transfer port 32. In this manner, the computer 34 can receive and/or send information from the VDD pin 48 and the VSS pin 50 separately. For example, through the output terminal 52, the computer 34 can monitor the current status of the power supply 26. Additionally, the output terminal 54 connected to the VSS pin 50 provides the computer 34 with a reference voltage to which the output signals from the microcontroller 46 can be compared.

The sensor 42 is shown in FIG. 4 as being a contact-sensitive switch operable between an ON and an OFF position. The sensor 42 is connected between a GP0 pin 56 and ground, such that when the membrane switch is closed, the GP0 pin 56 is grounded. Since the GP0 pin 56 is directly affected by the sensor 42, the GP0 pin 56 will also be referred to as the sensor state pin. An output terminal 58 is also connected to the GP0 pin 56 such that the microcontroller 46 can communicate with the computer 34 through the output terminal 58. In addition to functioning as the sensor state pin, the GP0 pin 56 will also be referred to as the data output pin since the microcontroller 46 is able to send its stored information to the external computer 34 through the GP0 pin 56.

As can be further seen in FIG. 4, a GP1 pin 60 is connected through output terminal 62 to the data transfer port 32. The GP1 pin 60 will be referred to as the read-out pin since it is used by the computer 34 to indicate to the microcontroller 46 that the stored information in the microcontroller 46 is to be sent to the computer 34. A GP2 pin 64 is connected to an output terminal 66 such that the GP2 pin 64 can communicate with the external computer 34 through the data transfer port 32. The GP2 pin 64 functions as a data strobe pin such that the external computer 34 will know when valid data is present on the GP0 pin 56 of the microcontroller 46.

An external oscillator 68 is attached to the microcontroller 46 in the preferred embodiment of the invention. Although the microcontroller 46 selected in the preferred embodiment includes an internal timing feature, the external oscillator 68 provides more accurate and reliable timing. The external oscillator 68 includes a quartz oscillator 69 and a pair of capacitors 70 and 71. The external oscillator 68 is connected between the two oscillator pins 72 and 74 on the microcontroller 46. The more reliable timing of the external oscillator 68 can be important in applications in which the bandage 10 is used for long durations. However, the oscillator contained within the microcontroller 46 can be utilized while still operating within the scope of the invention. A master clear line reset (MCLR) pin 76 is connected to an output terminal 78. The external computer 34 can supply a reset signal to the microcontroller 46 through the MCLR pin 76, the importance of which will be discussed below.

Although not shown in the Figures, it is contemplated by the inventors to include an indicator on the bandage 10 that would be coupled to the microcontroller 46. The indicator would be activated by the microcontroller based on the information received by the microcontroller 46 from the sensor 42 such that the microcontroller 46 could indicate to the patient that some predetermined condition exists. For example, the indicator could be a visual or audio alarm that indicates to the patient that the status of the bandage 10 or the patient's monitored region has reached a critical condition and immediate action should be taken.

Figure 5:
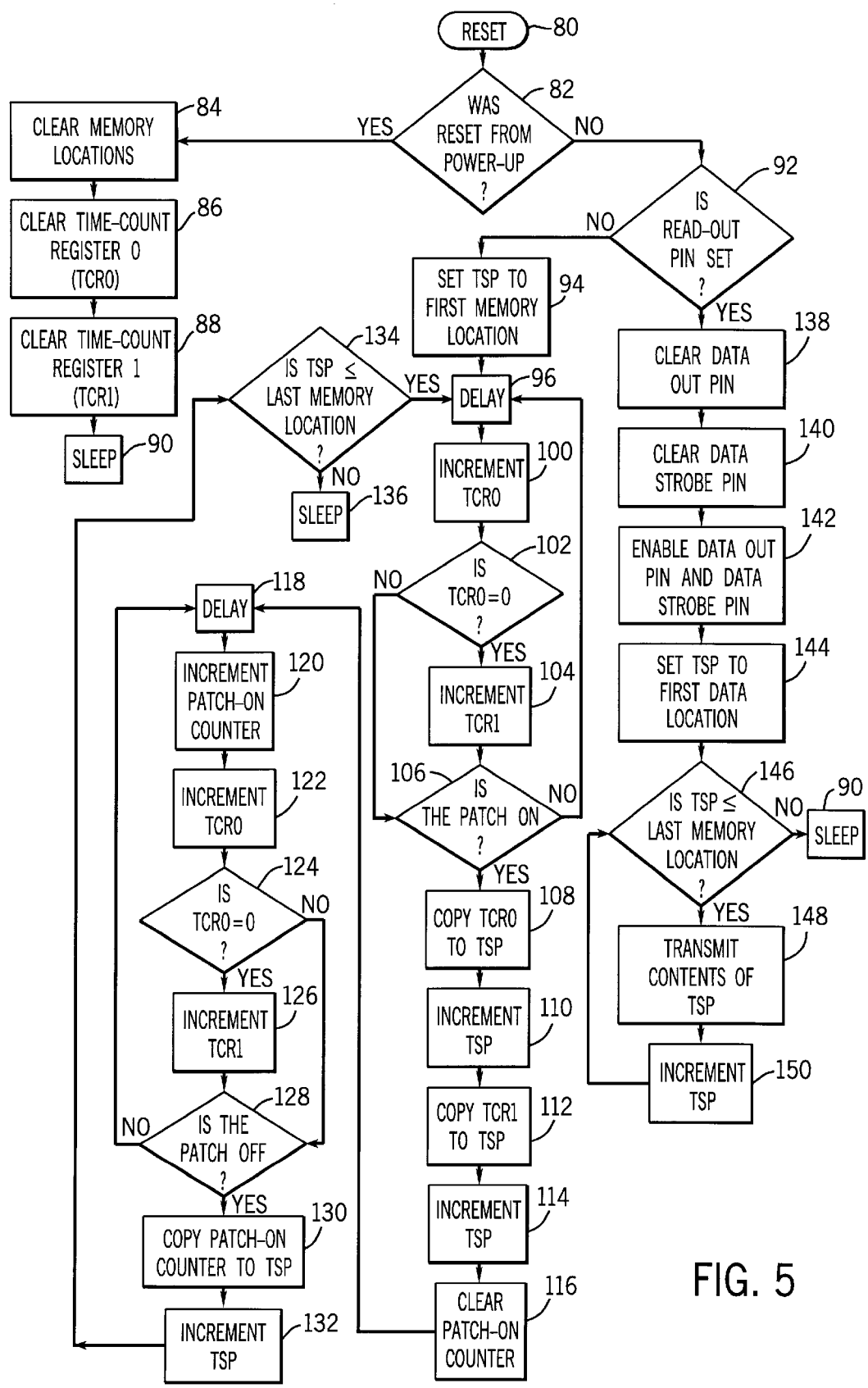
FIG. 5 is a flowchart of the operating software for the bandage of the invention.

FIG. 5 shows a flowchart depicting the internal operating program stored within the microcontroller 46 that determines how the microcontroller 46 operates. Although the flowchart in FIG. 5 describes one method of programming and operating the microcontroller 46, it should be understood that a variety of methods of operating the microcontroller 46 could be utilized while still operating under the scope of the present invention. Initially, after power is applied, the microcontroller 46 is reset and then enters the SLEEP mode, during which time the microcontroller 46 requires a low amount of power. In this manner, the microcontroller 46 reduces the amount of power drawn from the power supply 26 to extend the life of the power supply 26. The microcontroller 46 leaves the SLEEP mode when a reset signal is received, as shown by step 80. When a reset signal is received, the microcontroller 46 determines whether the reset was from power-up at step 82 or from the master clear line (MCLR) 76.

If the microcontroller 46 determines that the reset was received from power being supplied to the microcontroller 46 at step 82, the microcontroller 46 performs a series of steps which clear the registers contained within the microcontroller 46. For instance, the microcontroller 46 clears all of the memory locations in which the state change times will be stored within the memory of the microcontroller 46, as shown at step 84. After the memory locations have been cleared, the microcontroller 46 clears the first time count register TCR0 at step 86. The first time count register TCR0 is an 8-bit register that stores the lower half of a 16-bit unit time counter. After clearing the first time count register TCR0, the microcontroller 46 clears the second time count register TCR1 at step 88. The second time count register TCR1 is an 8-bit register that is used to store the upper half of the 16-bit unit time counter. After clearing the memory locations and time count registers, the microcontroller 46 enters the SLEEP mode at step 90 to conserve power.

If the reset signal was received from the MCLR pin 76, the microcontroller 46 then analyzes whether the read-out pin is set, as shown by step 92. Referring back to FIG. 4, the read-out pin corresponds to the GP1 pin 60 on the microcontroller 46. If the read-out pin is set, the microcontroller 46 downloads its stored data to the computer 34, as will be discussed later. If the read-out pin is not set, the microcontroller 46 begins monitoring and recording the status of the sensor 42.

In the preferred embodiment of the invention, the power is supplied to the eye patch 12 before the eye patch 12 is attached to the patient. For this reason, the microcontroller 46 initially assumes that the bandage 10 is not on the patient, the importance of which will be discussed below.

The first step in monitoring the status of sensor 42 is to set the time save pointer (TSP) to the first memory location in the microcontroller 46, as shown by step 94. In the preferred embodiment of the invention, the microcontroller 46 has forty-one 8-bit memory locations. After setting the TSP to the first memory location to be used for data storage, the microcontroller 46 delays for a specified period of time, as shown by step 96. In the preferred embodiment of the invention, the delay time at step 96 is ten minutes.

After the delay at step 96, the microcontroller 46 increments the first time count register TCR0, which represents the lower half of the unit time counter, at step 100. Once the TCR0 register has been incremented, the microcontroller 46 determines whether the TCR0 register has exceeded its maximum count value and cycled back to zero, as shown in step 102. If the TCR0 register has exceeded its maximum count value and is at zero, the microcontroller 46 increments the second time count register TCR1, which represents the upper half of the unit time counter, at step 104. Since the pair of registers TCR0 and TCR1 combine to represent a single 16-bit unit time counter, the pair of registers are incremented in a standard fashion to represent increasing binary numbers.

After incrementing the time count registers in the appropriate manner, the microcontroller 46 determines at step 106 whether the eye patch 12 has been applied to a patient. The microcontroller 46 makes this determination by monitoring the state of the sensor 42. In the preferred embodiment of the invention, the sensor 42 is a contact-sensitive switch operable between an ON and OFF state so the microcontroller 46 determines whether the sensor 42 is ON or OFF. If the state of the sensor 42 has not changed, the microcontroller 46 again delays at step 96 and begins the process of incrementing the registers as previously discussed. In this manner, the microcontroller 46 establishes a time frame based on counting the number of delays 96 since the MCLR reset was detected by the microcontroller 46.

If the microcontroller 46 determines that the eye patch 12 has been placed on the user at step 106, the microcontroller 46 copies the first time count register TCR0 to the memory location currently addressed by the time save pointer (TSP) at step 108. Since the memory location addressed by the TSP is an 8-bit register, the TSP is incremented at step 110 and the second half of the unit time counter (TCR1) is saved into the next 8-bit register addressed by the TSP at step 112. In this manner, the complete unit time counter comprised of both the 8-bit TCR0 and the 8-bit TCR1 are stored in consecutive 8-bit registers. Thus, the time at which the eye patch 12 was placed on the patient is stored in the microcontroller 46 in consecutively addressed memory locations. The values stored in these memory locations represent the number of delays 96 which occurred since the MCLR reset was detected by the microcontroller 46. After the time count registers TCR0 and TCR1 have been stored in the memory locations in the microcontroller 46, the TSP is incremented at step 114 to the next unused memory location.

Since the eye patch 12 is now on the user, the microcontroller 46 clears a patch-on counter at step 116. After clearing the patch-on counter, the microcontroller 46 delays for a specified period of time, as shown by step 118. As with delay 96, the delay 118 is ten minutes in the preferred embodiment of the invention. After the delay 118, the microcontroller 46 increments the patch-on counter at step 120. After incrementing the patch-on counter, the microcontroller 46 then increments the first time count register TCR0 at step 122. Once the TCR0 register has been incremented, the microcontroller 46 determines at step 124 whether the TCR0 register has exceeded its maximum count value and cycled back to zero. If the TCR0 register is zero, the microcontroller 46 increments the second time count register TC1 at step 126. By repeatedly incrementing the time count registers TCR0 and TCR1 regardless of whether the eye patch 12 is on or off, the microcontroller 46 generates a time line related to when the eye patch 12 was initially activated.

After incrementing the time count registers in the appropriate manner, the microcontroller 46 again determines whether the eye patch 12 is now on or off. If the state of the sensor 42 has not changed, thereby indicating the eye patch 12 is still on, the microcontroller 46 again delays at step 118 and begins the process of incrementing the register as discussed. In this manner, the microcontroller 46 counts the number of delay intervals (step 118) between the status change in the sensor 42.

If the sensor state has changed at step 128, this indicates that the eye patch 12 has been taken off after having been positioned on the user. Once the eye patch 12 has been taken of the patient, the microcontroller 46 copies the patch-on counter to the memory location corresponding to the TSP as shown in step 130. The patch-on counter signifies the number of delay periods which have occurred since the eye patch was placed on the user. For example, if the patch-on counter is four, this signifies that the eye patch 12 has been on for four (4) ten minute intervals, or forty minutes. Since the patch-on counter is an 8-bit register, the maximum count the patch-on counter can reach is 255, which signifies the eye patch 12 has been on for approximately 42 hours. After the patch-on counter has been stored in the register corresponding to the current TSP, the TSP is incremented at step 132.

After the TSP has been incremented at step 132, the microcontroller 46 determines at step 134 whether the TSP is less than or equal to the last memory location in the microcontroller 46. If the TSP is greater than the last memory location, the microcontroller determines that its memory is full and thus stops monitoring the sensor 42 and enters the SLEEP state 136. If the TSP is not at the last memory location, the microcontroller again returns to the delay step 96 and monitors the amount of time the eye patch 12 is off of the patient.

In the control strategy depicted in FIG. 5, the microcontroller 46 stores data which can be interpreted to determine when and how long the eye patch 12 was worn by the patient. Specifically, the microcontroller 46 records the time at which the eye patch 12 was placed on the user by storing the time count registers TCR0 and TCR1 into memory locations addressed by the TSP. After the eye patch 12 is placed on the user, the microcontroller 46 counts the number of ten minute delays (step 118) which occur between the time the patch is placed on the user and the time at which the patch is removed from the user. The patch-on counter will then be stored in the next memory location following the position in which the time is stored at which the eye patch 12 was previously attached to the patient. After the patch-on counter is stored in memory, the next two memory locations in the microcontroller 46 will contain the unit time counter value for the time at which the eye patch 12 is again applied to the patient. In this manner, the amount of time the eye patch 12 is applied to the patient can be determined by interpreting the memory locations in order, since the memory locations will include information as to when the eye patch 12 was applied to the patient and how long the eye patch 12 was in place on the patient.

If, at step 92, the microcontroller 46 determines that the read-out pin is set, the microcontroller 46 will download its stored data from the memory locations to the computer 34. The first step in downloading the stored information is to clear the data-out pin at step 138. Referring back to FIG. 4, the data-out pin corresponds to the GP0 pin 56 on the microcontroller 46. Once the data-out pin is cleared, the microcontroller 46 clears the data strobe pin, which corresponds to the GP2 pin 64, at step 140. Once both the data-out pin and the data strobe pin are cleared, the microcontroller 46 enables each of these pins at step 142. With the data-out pin and the data strobe pin enabled, the time save pointer (TSP) is set to the first memory location used to store data at step 144. The microcontroller 46 then determines whether the TSP is less than or equal to the last memory location available within the microcontroller 46. If the TSP is less than or equal to the last memory location, as determined at step 146, the microcontroller 46 will transmit the memory location addressed by the TSP at step 148 to the computer 34. After the memory location has been transmitted, the TSP is incremented at step 150 and the microcontroller 46 will again determine whether the TSP is less than or equal to the last memory location. Once the TSP has reached the last memory location, the microcontroller 46 will then enter the SLEEP mode as shown by step 90. In this manner, the microcontroller 46 can output the complete data stored by the microcontroller 46 in the multitude of 8-bit registers included in the microcontroller 46 memory. In the embodiment of the invention shown, the data stored in the 8-bit registers is the time at which the eye patch 12 was placed on the user and the amount of time the eye patch 12 was then on the patient. In this manner, a complete history of the eye patch 12 use can be retrieved from the microcontroller 46.

Although the present invention has been described as storing and outputting data related to the time at which the eye patch 12 is placed on a user, it is contemplated by the inventors that the bandage 10 of the present invention could be modified to perform a variety of functions in which monitoring the status of a bandage would be important. By changing the type of sensor 42 used with the bandage 10, the user could modify the bandage 10 to perform a variety of functions, as has been discussed.

It is recognized that various equivalents, alternatives and modifications to the invention as described are possible. Such equivalents, alternatives and modifications should be considered to fall within the scope of the following claims.

We claim:

1. A bandage comprising:
a pad positionable in contact with a patient;
a microcontroller contained within the pad; and
a sensor coupled to the microcontroller to provide a signal to the microcontroller, the signal being related to the status of the pad, wherein the microcontroller records information related to the signal from the sensor.

2. The bandage of claim 1 wherein the sensor generates a signal having an upper limit and a lower limit.

3. The bandage of claim 1 wherein the sensor generates a first signal when the pad is in a first state, and the sensor generates a second signal when the pad is in a second state.

4. The bandage of claim 3 further comprising a timer coupled to the microcontroller for generating a time signal.

5. The bandage of claim 4 wherein the microcontroller records the time at which the signal from the sensor switches between the first signal and the second signal.

6. The bandage of claim 3 wherein the sensor is a contact-sensitive sensor adapted to be positioned between an adhesive strip and the patient.

7. The bandage of claim 1 further comprising an indicator coupled to the microcontroller such that the microcontroller can activate the indicator based on the signal from the sensor.

8. The bandage of claim 1 further comprising a data transfer port formed in the pad, the data transfer port allowing for an external connection to the microcontroller contained within the pad.

9. The bandage of claim 1 wherein the pad is substantially opaque.

10. The bandage of claim 1 further comprising a power supply connected to the microcontroller, the power supply being contained in the pad.

11. An eye patch for use in occlusion therapy, the eye patch comprising:

a pad;

a microcontroller contained within the pad, the microcontroller having a memory capable of storing information;

means for attaching the eye patch to an eye area of a patient; and a sensor coupled to the microcontroller, the sensor providing a signal to the microcontroller, the signal from the sensor indicating whether the eye patch is attached to the patient, wherein the microcontroller records information related to the signal from the sensor in the memory.

12. The eye patch of claim 11 further comprising a power supply connected to the microcontroller, the power supply being contained within the pad.

13. The eye patch of claim 11 further comprising a data transfer port formed in the pad, the data transfer port allowing for an external connection to the microcontroller, wherein information can be transferred into and out of the microcontroller through the data transfer port.

14. The eye patch of claim 11 wherein the means for attaching the pad to a patient is at least one adhesive strip.

15. The eye patch of claim 11 wherein the sensor is a contact-sensitive sensor positioned between the means for attaching and the patient, such that the sensor generates a first signal when the eye patch is in contact with the patient, and the sensor generates a second signal when the eye patch is out of contact with the patient.

16. The eye patch of claim 15 further comprising a timer coupled to the microcontroller wherein the microcontroller records the time at which the signal from the sensor switches between the first signal and the second signal such that the microcontroller records when the eye patch is in contact with the patient.

17. The eye patch of claim 16 wherein the timer an oscillator which is contained within the pad and external to the microcontroller.

18. The eye patch of claim 11 further comprising:

a protective shield having a front and a back, the pad being attached to the front of the shield; and a cushion member attached to the back of the shield such that the cushion member is adapted to contact the patient.

19. An eye patch for use in occlusion therapy, the eye patch comprising:

a pad;

a programmable microcontroller contained within the pad, the microcontroller having a memory capable of storing information;

means for attaching the pad to a patient over an eye area of the patient;

a power supply connected to the microcontroller and contained within the pad;

a sensor coupled to the microcontroller, the sensor generating a first signal when the eye patch is in contact with the patient, and a second signal when the eye patch is out of contact with the patient;

a data transfer port formed in the pad, the data transfer port allowing for an external connection to the microcontroller such that information can be transferred into and out of the microcontroller through the data transfer port; and a timer contained within the pad and coupled to the microcontroller, the timer generating a time-dependent signal, wherein the microcontroller records the time at which the signal from the sensor switches between the first signal and the second signal, such that the microcontroller records when the eye patch is in contact with the patient relative to the time signal generated by the timer.

20. The eye patch of claim 19 further comprising:

a protective shield having a front and a back, the pad being attached to the front of the shield; and a cushioned member attached to the back of the shield such that the cushioned member is adapted to contact the patient.

21. A method of monitoring a patient wearing a bandage, the method comprising the steps of:

positioning a microcontroller within the bandage;

securing the bandage to the patient at a desired location;

attaching a sensor to the microcontroller;

positioning the sensor such that the sensor generates a signal based on the status of the patient and the bandage;

monitoring the signal generated by the sensor; and recording in memory in the microcontroller information desired from the signal generated by the sensor.

22. The method of claim 21 further comprising the step of activating a timer upon initially securing the bandage to the patient such that the timer forms a basis for determining when the bandage is secured to the patient.

23. The method of claim 21 further comprising the step of downloading the recorded information from the memory of the microcontroller to an external computer such that the recorded information stored within the microcontroller can be read.

24. The method of claim 21 further comprising the step of positioning a power supply within the bandage, the power supply providing power to the microcontroller.

25. A method of determining patient compliance in wearing an eye patch, the method comprising the steps of:

positioning a microcontroller within the eye patch;

securing the eye patch to the patient at the desired location;

attaching a sensor to the microcontroller;

positioning the sensor between the bandage and the patient such that the sensor generates a first signal when the bandage is in contact with the patient and generates a second signal when the bandage is not in contact with the patient;

monitoring the signal generated by the sensor;

determining when the signal from the sensor changes between the first signal and the second signal; and recording in a memory in the microcontroller the time at which the signal from the sensor changes.

26. The method of claim 25 further comprising the step of activating a timer upon initially securing the eye patch to the patient, such that the timer forms a basis for determining when the eye patch is in contact with the patient.

27. The method of claim 25 further comprising the step of downloading the recorded information from the memory of the microcontroller to an external computer, such that the recorded information stored within the microcontroller can be read.

28. The method of claim 25 further comprising the step of positioning a power supply within the eye patch the power supply providing power to the microcontroller and the sensor.

29. The method of claim 25 wherein the step of attaching the sensor comprises attaching a contact-sensitive sensor.

* * * * *